United States Patent [19]

Barak et al.

[11] Patent Number: 5,428,063

[45] Date of Patent: Jun. 27, 1995

[54] USE OF BETAINE AS A HEPATIC GENERATOR OF S-ADENOSYLMETHIONINE AND AS A PROTECTIVE AGENT AGAINST HEPATOTOXICITY

[75] Inventors: Anthony J. Barak, Elkhorn; Dean J. Tuma; Harriet C. Beckenhauer, both of Omaha, all of Nebr.

[73] Assignee: Board of Regents of the University of Nebraska, Lincoln, Nebr.

[21] Appl. No.: 225,819

[22] Filed: Apr. 11, 1994

[51] Int. Cl.6 .............................................. A61K 31/195
[52] U.S. Cl. ...................................... 514/556; 562/573
[58] Field of Search ......................... 514/556; 562/573

[56] References Cited

U.S. PATENT DOCUMENTS 3,242,048  3/1966  Straub et al. ........................... 167/55

OTHER PUBLICATIONS

Barak, 1993, Dietary Betaine Promotes Generation of Hepatic S-Adenosylmethionine and Protects the Liver from Ethanol-Induced Fatty Infiltration, *Alcoholism: Clinical and Experimental Research*, vol. 17; No. 3.
Barak, 1987, Effects of Prolonged Ethanol Feeding on Methionine Metabolism in Rat Liter, *Biochem Cell Biol.* vol. 65.
Beckenhauer, 1992, Effect of Betaine on Hepatic S-Adenosylmethionine (SAM) in Control and Alcohol-Fed Rats, *Alcoholism*, vol. 16, No. 3.
Beckenhauer, 1993, Relationship of Administered Dietary Levels of Betaine to Hepatic S-Adenosylmethionine and Triglyceride, *Hepatology*, vol. 18, No. 4, Pt. 2.
CA: 71:80801r–Logeais (1969).

*Primary Examiner*—Marianne M. Cintins
*Assistant Examiner*—T. J. Criares
*Attorney, Agent, or Firm*—Zarley, McKee, Thomte, Voorhees, & Sease

[57] ABSTRACT

This invention encompasses pharmaceutical compositions in the dietary supplement for treating or preventing fatty infiltration, the first stage of cirrhosis of the liver comprising and administering of not less than 1500 mg of betaine per kg of body weight per day. Dietary supplementation of betaine was shown to completely protect against liver fatty infiltration in rats exposed to prolonged ethanol intake as well as carbon tetrachloride. Hepatic levels of SAM were also elevated, which suggests the mechanism for the protection of the liver.

9 Claims, 2 Drawing Sheets

USE OF BETAINE AS A HEPATIC GENERATOR OF S-ADENOSYLMETHIONINE AND AS A PROTECTIVE AGENT AGAINST HEPATOTOXICITY

FIELD OF THE INVENTION

This invention relates to the field of treating liver cirrhosis caused by alcohol or other hepatotoxic agents.

BACKGROUND OF THE INVENTION

Ethanol is an extremely potent hepatotoxin and can lead to cirrhosis of the liver upon prolonged exposure. In fact 20% of chronic alcoholics will eventually experience cirrhosis. The process of cirrhosis of the liver involves a series of steps beginning with fatty infiltration which leads to necrosis or cell death, then fibrosis which in turn leads to cirrhosis.

During the initial stage, fatty infiltration, fat which is formed in the liver as a metabolic product of alcohol, begins to accumulate in the liver. This is a transient stage and is reversible upon reduction in ethanol ingestion, however, it will remain and accumulate in the liver upon continued ethanol exposure. When the fatty infiltration gets to a level of 30-40%, the liver becomes enlarged. Following this, some unknown change occurs. The fat begins to leave the liver and is replaced by the abnormal formation of scar tissue in a connective tissue framework. Eventually the scar tissue becomes hard and nodular and this is the stage termed cirrhosis of the liver. When cirrhosis has occurred to approximately 6/7th of the liver, the patient will pass into a stage of hepatic coma and eventually will die.

There are no known cures or treatments for cirrhosis. Once the patient's liver has turned from fatty infiltration to the step of fibrosis, the changes in the liver are irreversible. Current treatment methods involve therapies to relieve some of the symptoms, however, they do not stop the progression. Much study has been devoted to the progression of cirrhosis of the liver with relatively little advance in understanding.

Since there are no effective treatments for liver cirrhosis, it goes without saying there is a need for one. This is particularly true for those addicted to alcohol who by force of the addiction will continue the habit that leads to liver damage. A treatment which would prevent alcohol damage to the liver would be desirable, especially for those whose habits require constant subjection of the liver to alcohol abuse.

In the past, there have been no treatments to prevent the liver damage caused by alcohol. The present invention is therefore fulfilling a need for an effective treatment, in fact the invention virtually prevents the initial stage of cirrhosis from occurring upon exposure to alcohol.

The invention is predicated, at least in part, upon the inventors' knowledge of the metabolic pathways in the body and their experiences with liver function.

It is the object of the present invention to provide a betaine supplement for the diet which will protect the liver against fatty infiltration and advanced liver injury due to ethanol and other hepatotoxins, such as carbon-tetrachloride.

SUMMARY OF THE INVENTION

This invention encompasses pharmaceutical compositions containing betaine and a method for using betaine supplementation for prevention and treatment of liver fibrosis and cirrhosis. These agents and methods are particularly applicable for the treatment of individuals who consume excess alcohol. The compositions will act to markedly reduce fatty infiltration of the liver and thus halt the further stages of liver damage.

DETAILED DESCRIPTION OF THE INVENTION

Figure 1:
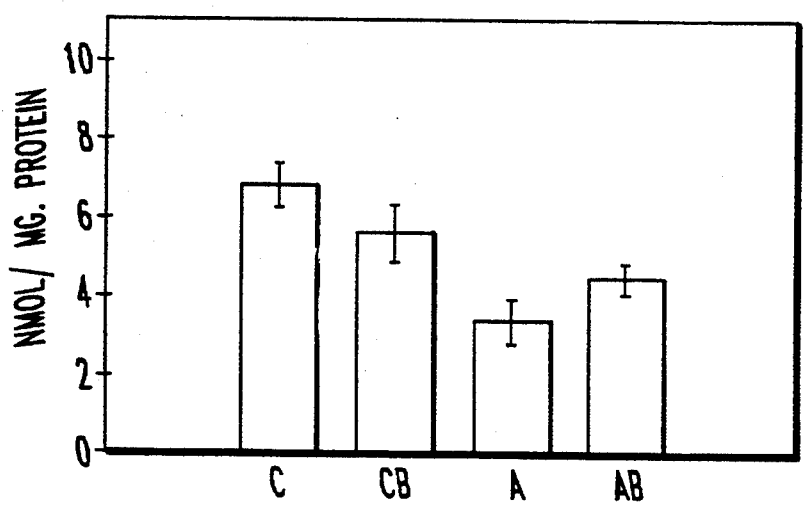
FIG. 1 is a bar graph depicting the effect of alcohol feeding and dietary betaine supplementation on Methionine Sinthetase (MS) in the liver (means±SEM). This enzyme was assayed in a cytosolic preparation, and activity is expressed on the basis of protein in this preparation. C is control diet; CB is control diet+betaine; A is alcohol diet; AB is alcohol diet+betaine. In comparison with C by Student's t test: CB is not significant; A-$p<0.001$; AB-$p<0.01$.

Betaine has the following generally recognized structure:

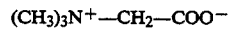

$$(CH_3)_3N^+—CH_2—COO^-$$

It is a natural substance and is found in some amount in all organisms, as well as in some dietary sources such as beets, broccoli and a few other vegetables. Derivatives of betaine are used industrially for improved thickening and foam boosting properties in cosmetics according to U.S. Pat. No. 4,490,355; in an antimicrobial skin cleansing composition according to reissue U.S. Pat. No. 32,300 and in U.S. Pat. No. 4,130,637. Betaine compounds derived from higher alkyl dimethyl carboxylic acid quaternary ammonium compounds were found effective in controlling dental plaque without discoloration of tooth surfaces.

Endogenously, betaine is an oxidation product of choline catalyzed by the enzyme choline oxidase. As such betaine is involved in the complex metabolism and biosynthesis of amino acids, as it occurs primarily in the liver. Betaine is a substrate of betaine homocysteine methyl transferase (BHMT) an alternate enzyme for methionine formation through the methylation of homocysteine. The conversion of homocysteine to methionine is an essential reaction from the standpoint of conserving methionine, detoxifying homocysteine, and most importantly in producing S-adenosylmethionine (SAM) the principle methylating agent in the body. SAM is critical to several biochemical and metabolic pathways and its numerous functions and interactions are not completely understood. SAM has been used successfully as a therapeutic agent in several human maladies such as Alzheimer's disease, treatment of migraine headaches, epilepsy, and osteoarthritis.

Traditionally the conversion of homocysteine to methionine occurs via the enzyme methionine synthetase. In the reaction, $N^5$-methyltetrahydrofolate donates a methyl group to homocysteine resulting in the amino acid methionine.

It has been shown by previous studies that the enzyme methionine synthetase is inhibited by extended exposure to the hepatotoxin ethanol (Barak, A. J.; Beckenhauer, H. C.; Tuma, D. J.; Badaksh, S; (1987) Effects Of Prolonged Ethanol Feeding In Methionine Metabolism In Rat Liver, Biochem. Cell Biol 65:230–233). Concomitant with the inhibition of methionine synthetase, BHMT was found to be stimulated.

According to the present invention, it was found that administration of betaine in dose effective amounts to animals subjected to cirrhosis-causing conditions such as the hepatotoxins ethanol or carbon tetrachloride, resulted in resistance to the development of cirrhosis of the liver by allowing virtually no fatty infiltration.

While not wishing to be bound by any theory, it is postulated that the administration of dose effective amounts of betaine in the presence of alcohol or other hepatotoxins allows for utilization of the alternate methionine synthesis pathway via BHMT and allows for maintenance and even elevation of critical SAM levels while also protecting the liver from fatty infiltration.

This is particularly significant for humans and other higher mammals, for although they have the substrates and enzymes for use of this betaine pathway, they do not possess the liver enzyme choline oxidase for endogenous production of betaine from choline and must rely on purely dietary sources for the product. This could render humans more vulnerable to the toxic effects of alcohol than rats, who have hepatic choline oxidase.

The betaine amount required is dose effective in preventing fatty infiltration. It was found that administration of betaine orally at levels of 1500 mg per kg of body weight per day was the minimum level of betaine necessary to achieve a protective effect. There is virtually no limit on upper levels of betaine as no toxicity to the compound is known. Levels less than 1500 mg per kg per day of body weight did not substantially protect livers from fatty infiltration.

The invention contemplates administration of small but protective amounts of betaine to guard against the early stages of liver cirrhosis.

The betaine may be administered orally as a diet supplement or through any other method so that it will eventually reach the liver. The invention also contemplates a pharmaceutical composition comprising betaine and a pharmaceutical carrier.

Any pharmaceutical carrier may be used so long as it does not react with the betaine itself. The usual pharmaceutical compounding agents, diluents or carriers may be included in these compositions as desirable for the particular route of administration and dosage form. The amount and type of diluent or carrier used should, of course, be compatible with the active compound of this invention. For instance, a cosolvent or other standard adjuvant, such as a surfactant, may be necessary to maintain the agent in solution or suspension at the desired concentration.

Pharmaceutical carriers which are liquid or solid may be used. The preferred liquid carrier is water. Flavoring materials may be included in the solutions as desired.

Solid pharmaceutical carriers such as starch, sugar, talc, mannitol and the like may be used to form powders. Mannitol is the preferred solid carrier. The powders may be used as such for direct administration to a patient or, instead, the powders may be added to suitable foods and liquids, including water, to facilitate administration.

The powders also may be used to make tablets, or to fill gelatin capsules. Suitable lubricants like magnesium stearate, binders such as gelatin, and disintegrating agents like sodium carbonate in combination with citric acid may be used to form the tablets.

Unit dosage forms such as tablets and capsules may contain any suitable predetermined amount of one or more of the phenylalkylhydrazines, advisably as a non-toxic acid addition salt, and may be administered one or more at a time at regular intervals. Such unit dosage forms, however, should generally contain a concentration of 0.1% to 10% by weight of one or more of the active hydrazines.

A typical tablet may have the composition:

|  | Mg. |
| --- | --- |
| 1. Chloramphenicol acetonide | 12.5 |
| 2. Mannitol | 100 |
| 3. Stearic acid | 3 |

A granulation is made from the mannitol. The other ingredients are added to the dry granulation and then the tablets are punched.

Another tablet may have the composition:

|  | Mg. |
| --- | --- |
| 1. Chloramphenicol acetonide | 10 |
| 2. Starch U.S.P. | 57 |
| 3. Lactose U.S.P. 73 | |
| 4. Talc U.S.P. | 9 |
| 5. Stearic acid | 6 |

Powders 1, 2 and 3 are slugged, then granulated, mixed with 4 and 5, and tableted.

Capsules may be prepared by filling No. 3 hard gelatin capsules with the following ingredients, thoroughly mixed:

|  | Mg. |
| --- | --- |
| 1. Chloramphenicol acetonide | 5 |
| 2. Lactose U.S.P. | 200 |
| 3. Starch U.S.P. | 16 |
| 4. Talc U.S.P. | 8 |

Such carrier materials are well known to those skilled in the art of pharmaceutical formulations. For those not skilled in the art, reference is made to the text entitled, "REMINGTON'S PHARMACEUTICAL SCIENCES," 17th edition, 1985, ed. Alfonso R. Gennaro, Mack Publishing Company, Easton, Pa. 18042.

EXAMPLE 1

BETAINE EFFECT ON ALCOHOLIC CHANGES IN LIVER

In prior studies it was found that short term and prolonged feeding of ethanol to rats effected methionine metabolism by reducing MS activity. Additionally and possibly to compensate for the decrease of MS activity, the activity of BHMT the alternate enzyme for methionine formation was induced. Further, hepatic betaine levels were reduced. Levels of SAM were maintained at normal levels for two months despite the decrease in methionine synthetase however SAM levels gradually diminished upon prolonged ethanol intake. While not wishing to be bound by any theory, it is suggested that higher mammals, such as humans, certain species who do not produce choline oxidase and produce little betaine from choline, may be more susceptible to detrimental effects of ethanol in the liver as compared with rats because they lack sufficient levels of betaine for the synthesis of methionine via BHMT.

Accordingly, betaine was supplemented in the diet of rats, who were exposed to ethanol. Male Sprague-Dawley rats (~180 g) were divided into four groups (six animals per group) and housed separately. Group 1 was fed the Lieber et al (Lieber, C. S., Jones D. P., DeCarli L. M. (1989 update), Liquid Diet Technique of Ethanol Administration, Alcohol Alcoholism 24:197–211) semi-liquid control diet (C). Group 2 was fed the same diet to which had been added betaine in the amount of 0.5% (weight/volume)(CB). Group 3 was fed the Lieber et al. semiliquid ethanol diet (A), and group 4 was fed the ethanol diet containing the 0.5% betaine (AB). Rats in groups 1–3 were group-fed the amount of diet consumed by rats in group 4 to ensure isocaloric intake of all rats in all groups.

Rats were maintained with this dietary regimen for 4 weeks, after which they were killed in tile nonfasting state. Livers taken were freeze-clamped at −70° C. and stored at this temperature until analyzed. Total fat was extracted from the livers by the chloroform:methanol method of Folch et al, (Folch J., Lees M., Stanley G. H. S. (1957): A Simple Method for the Isolation and Purification of Total Lipids From Animal Tissues. *J. Biol. Chem.* 226:497–509) and triglycerides in the extract were then saponified and quantitated using the diagnostics kit no. 320-UV of the Sigma Chemical Company (St. Louis, Mo.). Hepatic betaine levels were measured according to Barak and Tuma (Barak A. J., Tuma D. J. (1979): A Simplified Procedure for the Determination of Betaine in Liver. *Lipids* 14:860–863) and liver SAM was estimated by the procedure of Eloranta et al. (Eloranta T. O., Kajander E. O., Paina A. M., (1976): A New Method for the Assay of Tissue S-Adenosylmethionine and S-Adenosylhomocysteine. *Biochem J.* 160:287–294). The enzyme, MS, was assayed by the methods of Mudd et al. (Mudd S. H., Levy H. L., Morrow G. III, (1970): Deranged B12 Metabolism: Effect of Sulfur Amino Acid Metabolism. *Biochem Med* 4:193–214) using the Dowex column means of separating methionine. BHMT was measured by the method of Ericson and Harper (Ericson L. E., Harper A. E., (1956): Effect of Diet on the Betaine-Homocysteine Transmethylase Activity in Rat Liver. *J. Biol. Chem* 219-49–58). Hepatic protein was measured according to Lowry et al (Lowry O. H., Rosenbrough N. J., Farr A. L., Randall R. J., (1951): Protein Measurement With the Folin Phenol Reagent. *J Biol Chem* 193:265–275).

Table 1 lists the initial and final body weights of the animals in this study and the liver weights per 100 g of body weight at the time of killing.

TABLE 1

Means (± SEM) Initial Body weights and Final Body Weights and Liver Weights of Rats in Ethanol-Betaine Study

| Group | No. of Animals | Initial body wt. (g) | Final body wt. (g) | Mean liver Wt. (g)/100 g body wt. |
|---|---|---|---|---|
| Control | 6 | 183.8 ± 8.4 | 219.8 ± 4.2 | 2.80 ± 0.07 |
| Control-betaine | 6 | 182.3 ± 5.4* | 222.3 ± 4.4* | 3.08 ± 0.10* |
| Ethanol | 6 | 187.8 ± 6.7* | 162.7 ± 5.5† | 4.28 ± 0.12† |
| Ethanol-betaine | 6 | 183.2 ± 6.1* | 180.6 ± 8.0# | 4.24 ± 0.15† |

Statistical comparison with the control group using Student's t test: *not significant; † $p < 0.001$; # $p < 0.002$.

The control animals gained weight throughout the study, and dietary betaine supplementation had no effect on this. Even though receiving the same caloric intake as the other groups, the ethanol-fed group alone lost body weight, but betaine supplementation prevented this weight loss.

Betaine in the control diet did not effect liver weight. The ethanol diet produced an increase in liver weight (hepatomegaly), but even though it prevented body weight loss in ethanol-fed animals, betaine supplementation did not protect against the hepatomegaly.

FIG. 1 demonstrates the effect of ethanol feeding and dietary betaine supplementation on hepatic methionine synthetase activity. As in earlier studies, this demonstrated lowered activity of the enzyme in the presence of alcohol. The feeding of betaine had little effect on MS activity in control animals and did not prevent alcoholic reduction of MS.

Figure 2A:
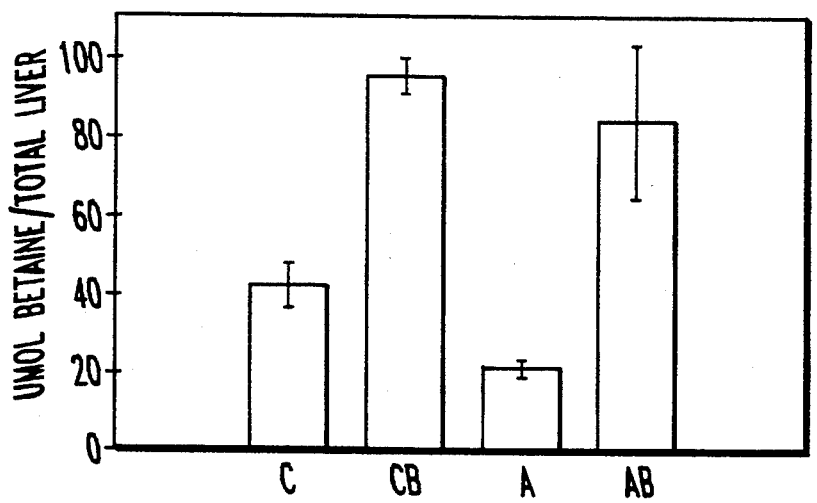
FIG. 2a is a bar graph depicting the hepatic effect of dietary betaine supplementation on hepatic betaine. In comparison with C by Student's t test: CB-$p<0.001$; A-$p<0.01$; AB-$p<0.05$.

Ethanol feeding lowered endogenous hepatic betaine levels from those observed in the control animals, but the dietary supplementation of betaine elevated hepatic levels of this substance in both the control and ethanol-fed rats (FIG. 2A).

Figure 2B:
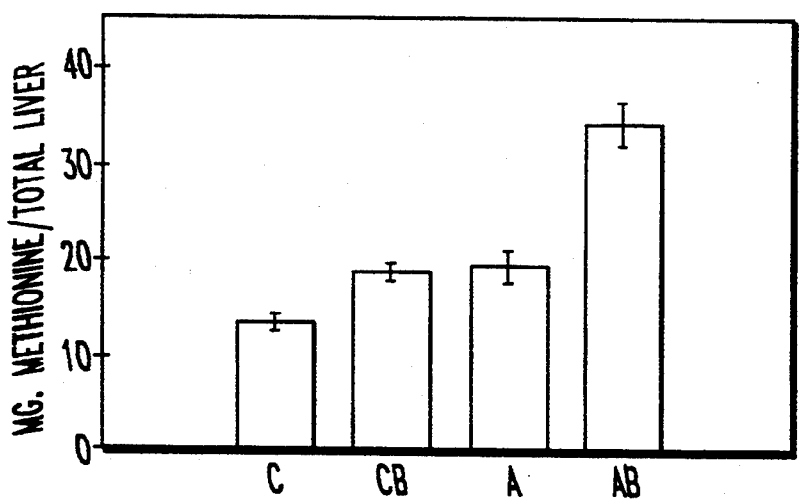
FIG. 2b is the effect of dietary betaine supplementation on betaine homocysteine methyl transferase (BHMT) activity in liver (means±SEM). BHMT activity is expressed in terms of methionine produced per g liver in a 3-hour incubation period. In comparison with C by Student's t test: CB-$p<0.002$; A-$p<0.01$; AB-$p<0.001$.

Additionally, ethanol feeding resulted in the elevation of BHMT activity in the liver and betaine supplementation increased BHMT activity in the control animals and further elevated the activity of this enzyme in the ethanol-fed rats (FIG. 2B).

Figure 3:
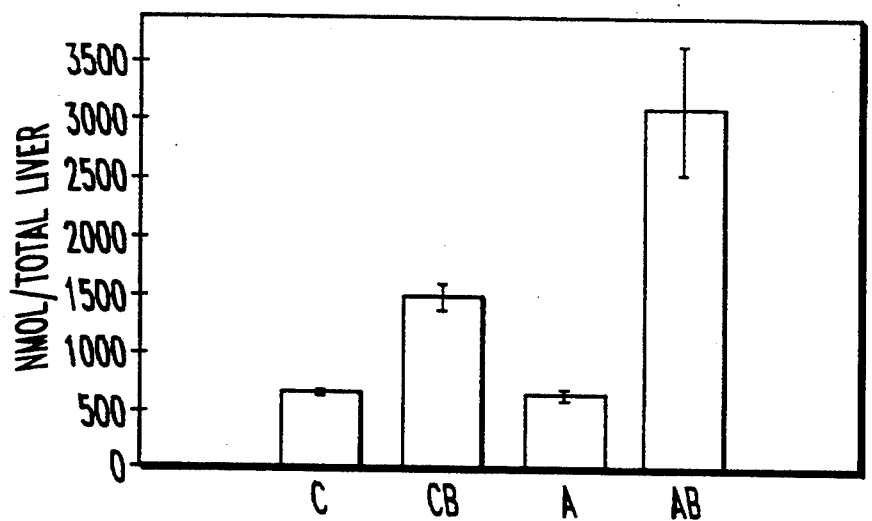
FIG. 3 is a bar graph depicting the effect of dietary betaine supplementation on hepatic SAM in control and ethanol-fed animals (means±SEM). In comparison with C by Student's t test: CB-$p<0.001$; A-not significant; AB-$p<0.001$.

FIG. 3 demonstrates that ethanol feeding for 30 days did not significantly lower the hepatic SAM levels in agreement with previous studies. However, administration of betaine caused a 2-fold elevation of hepatic SAM levels in the control rats and a marked 4-fold increase in the ethanol-treated rats (FIG. 3).

Figure 4:
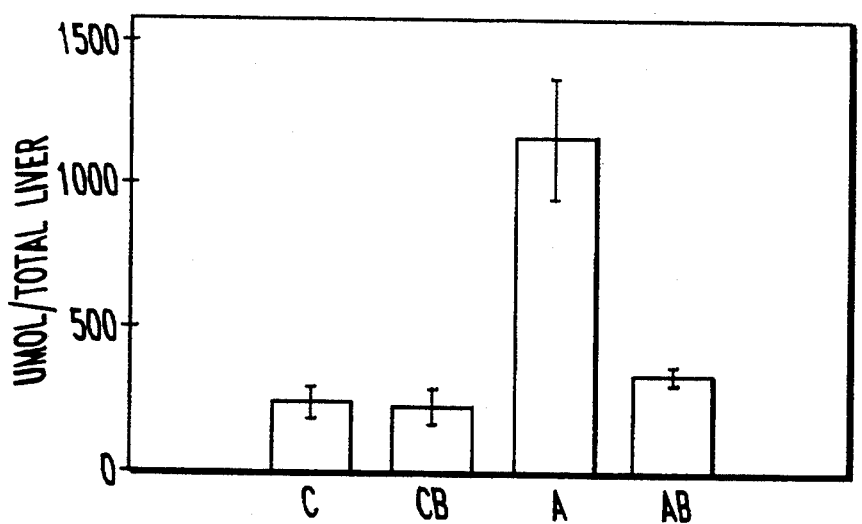
FIG. 4 is a bar graph depicting the effect of ethanol feeding and dietary betaine supplementation on hepatic triglyceride levels in liver (means±SEM). In comparison with C by Student's t test: CB-not significant; A-$p<0.002$; AB-not significant.

Betaine supplementation did not alter hepatic triglyceride levels in the control animals. However, quite unexpectedly, betaine did prevent the ethanol-induced increase in hepatic triglyceride accumulation (FIG. 4). Histological inspection of the livers (College of Veterinary Medicine, Helsinki, Finland) also demonstrated that betaine protected against an alcoholic fatty liver.

Folate metabolism has long been recognized as the major derangement caused by chronic ethanol consumption. Although this is so, the precise sites of these alterations have yet to be completely clarified. In conformity with other results the activity of MS, a folate-dependent enzyme, is decreased by chronic ethanol administration producing an accumulation of $N^5$- methyltetrahydrofolate, one of the substrates of this enzyme. It is hypothesized that the decreased activity of MS sets into action a series of events in the liver in order to compensate for decreased methionine synthesis. One such mechanism may be the ethanol-induced increase in BHMT activity that utilizes betaine as a substrate for the synthesis of methionine via the alternate pathway. This adaptation results in the conservation of methionine and more importantly, the essential methionine metabolite, SAM.

Dietary betaine supplementation increased hepatic levels of betaine in control and ethanol-fed rats, and also increased BHMT activity in control animals and further increased the already elevated activity of this enzyme in ethanol-fed animals. Hepatic SAM levels were increased in controls and were markedly elevated in livers of ethanol-fed rats. Thus despite decreased MS activity in the livers of ethanol-fed rats, increased betaine levels and enhanced BHMT activity resulted in increased methionine and subsequent SAM synthesis via the alternate pathway for methionine synthesis.

Quite unexpectedly accompanying the elevation of hepatic SAM levels, livers in the study were protected against infiltration of fat that results from ethanol ingestion.

While not wishing to be bound by any theory, it is well accepted that SAM is involved in protecting the liver from steatosis and further liver injury. The results here are of particular interest in that they show that supplemented, dietary betaine generates SAM and protects the liver even in a species, the rat, that can product its own betaine. In this light, these results would be significant in humans who have a limited capacity to synthesize betaine from choline and generate SAM. Hence, it is indeed highly feasible that betaine may well become a promising therapeutic agent in the treatment of human liver disease.

EXAMPLE 2

VARYING LEVELS OF DIETARY BETAINE

To determine the minimal levels of betaine which must be present to achieve the protective effect, levels of betaine at 0.05, 0.15, and 0.25 and 0.50 in semi-liquid control and alcohol diets were tested in rats for 30 days. Male Sprague-Dawley rats (~200 g) were divided into four large groups. Group 1 (C) was fed the Lieber et al. semiliquid control diet. Group 2 (CB) was fed the same diet to which betaine had been added. Group 3 (E) was fed the Lieber et al ethanol diet and group 4 (EB) was fed the ethanol diet containing betaine. Four different dietary levels of betaine (0.05, 0.10, 0.25, and 0.50% w/v) were tested. Each level was tested with all four dietary groups. At each level betaine supplemented rats in groups 1, 2, and 3 were group fed daily that amount of diet consumed by the animal in group 4 the previous day. This insured isocaloric intake of diet by all rats within each dietary betaine group throughout the course of the experiment.

Rats were maintained with this dietary regiment for four weeks after which they were killed in the nonfasting state. Livers were taken and freeze clamped at −70° C. and stored briefly at this temperature until analyzed. Once again total fat was extracted by the chloroform-:methanol method and triglycerides in the extract were quantitated using the diagnostics kit no. 320-UV of the Sigma Chemical Company (St. Louis, Mo.). Hepatic betaine levels were measured and liver SAM was estimated. The findings are illustrated in Tables 1, 2, and 3 which follow. The results with the 0.05 and 0.10 betaine levels were not shown because at this level of supplementation betaine did not influence the perameters studied.

TABLE 1

Effect of Differences in Dietary Betaine on Hepatic Betaine[1]

| Diet | Symbol | No. Animals in each diet group | Level of Dietary Betaine 0.25% | 0.50% |
|---|---|---|---|---|
| Control | C | 6 | 31.9 ± 2.2 | 43.1 ± 6.3† |
| Control + Betaine | CB | 6 | 77.1 ± 6.2 | 98.6 ± 4.6* |
| Ethanol | E | 6 | 22.2 ± 1.5 | 21.8 ± 2.1† |
| Ethanol + Betaine | EB | 6 | 40.0 ± 6.5 | 86.4 ± 20.3# |

[1] Values listed are in terms of $\mu$mol/total liver, means ± SEM
[2] In comparison with C by Student's t test for 0.25% diet: CB-p < 0.001; E-p < 0.01; EB-not significant.
For 0.50% diet: CB-p < 0.001; E-p < 0.01; EB-p < 0.02.
In comparison between 0.25% and 0.50% diets by Student's t test, † not significant, #p < 0.05, *p < 0.02.

TABLE 2

Effect of Differences in Dietary Betaine on Hepatic SAM[1]

| Diet | Symbol | No. Animals in each diet group | Level of Dietary Betaine 0.25% | 0.50% |
|---|---|---|---|---|
| Control | C | 6 | 1028 ± 44 | 911 ± 70† |
| Control + Betaine | CB | 6 | 2037 ± 158 | 1895 ± 68† |
| Ethanol | E | 6 | 768 ± 17 | 624 ± 71† |
| Ethanol + Betaine | EB | 6 | 1654 ± 181 | 3754 ± 418# |

[1] Values listed are in terms of nmol/total liver, means ± SEM
[2] In comparison with C by Student's t test for 0.25% diet: CB-p < 0.001; E-p < 0.001; EB-p < .01.
For 0.50% diet: CB-p < 0.001; E-p < 0.02; EB-p < 0.0001.
In comparison between 0.25% and 0.50% diets by Student's t test, † not significant, #p < 0.002.

TABLE 3

Effect of Differences in Dietary Betaine on Hepatic Triglyceride[1]

| Diet | Symbol | No. Animals in each diet group | Level of Dietary Betaine 0.25% | 0.50% |
|---|---|---|---|---|
| Control | C | 6 | 399 ± 40.9 | 355 ± 73.7† |
| Control + Betaine | CB | 6 | 371 ± 50.2 | 240 ± 40.9† |
| Ethanol | E | 6 | 2763 ± 971 | 1975 ± 618† |
| Ethanol + Betaine | EB | 6 | 2060 ± 458 | 521 ± 136# |

[1] Values listed are in terms of $\mu$mol/total liver, means ± SEM
[2] In comparison with C by Student's t test for 0.25% diet: CB-not significant; E-p < 0.02; EB-p < 0.01.
For 0.50% diet: CB-not significant; E-p < 0.01; EB-p < 0.05.
In comparison between 0.25% and 0.50% diets by Student's t test, † not significant, #p < 0.05.

Table 1 demonstrates that ethanol feeding reduces hepatic levels of betaine. The administration of betaine at the 0.25% level elevated hepatic betaine pools in control rats and prevented the decrease in betaine levels in the ethanol-fed group. Administration of betaine at the 0.5% level markedly elevated hepatic betaine pools in both the control and ethanol-fed animals to a much greater extent than the 0.25% level of supplementation.

Table 2 demonstrates that dietary ethanol slightly reduced hepatic SAM levels from that of controls. Supplying betaine at the 0.25% level increased the hepatic pool of SAM in control livers; however, in the ethanol-fed animals, SAM levels were increased to a lesser extent. At the 0.5% level of dietary betaine, hepatic SAM was doubled in control animals and elevated fourfold in ethanol-fed rats.

The administration of supplemental betaine at the 0.25% and 0.5% levels on hepatic triglyceride is indicated in Table 3. In control animals, the feeding of betaine at these concentrations had no effect on triglyceride. The triglyceride infiltration of the liver due to the feeding of ethanol was not changed by the feeding of 0.25% betaine; however, this infiltration was practically eliminated with the 0.5% dietary level. Thus it appears that a dietary level of 0.50% (1500 mg/kg per day) affords complete protection against steatosis, the early stage of alcohol injury.

EXAMPLE 3

BETAINE PROTECTION FROM FATTY INFILTRATION WITH HEPATOTOXIN CARBON TETRACHLORIDE

The protective effect of supplemental betaine in the diet was shown not only to prevent ethanol induced fatty infiltration but also that of carbon tetrachloride. This compound is a solvent used commercially and is highly toxic.

Four groups of rats of six animals each were placed in a study to determine the effects of carbon tetrachloride and the protective effects of betaine. The diet fed to the animals was again the normal Lieber-DeCarli diet and each rat was housed separately. All animals were fed isocalorically to make certain of the equal receipt of calories and betaine. Animals in group 1 were fed the diet for seven days. On the fourth day through the seventh day they each received subcutaneous injections of carbon tetrachloride and olive oil in a 40:60 mixture. Dosage given was 1 ml carbon tetrachloride/kg body weight.

Animals in group 2 were fed the same diet as above but containing 2% betaine for three days. Carbon tetrachloride in the dose above was then administered on the fourth day through the seventh day while the betaine containing diet was continued throughout this period.

Animals in group 3 merely received the normal Lieber-DeCarli diet for seven days. This was a control group. Group 4 received the 2% betaine diet for three days. Afterwards they were continued on the diet while daily receiving subcutaneous injections of pure olive oil equivalent to the volume of their counterpart in group 2 for four more days. This was the betaine:olive oil control group. At the end of the seven days the animals were killed and livers analyzed for perimeters of methionine metabolism.

It was shown that carbon tetrachloride produced four times the level of fat in the liver compared to the controls. This amount of fatty infiltration was completely eliminated by the 2% betaine in the diet. Thus it is clear that the protective effect of betaine is not simply limited to ethanol induced fatty infiltration. From all of the foregoing it can be seen that the invention accomplishes the objectives of showing that betaine not only is a biological generator of SAM, but protects the liver against two of the most devastating hepatoxins, ethanol and carbontetrachloride.

What is claimed is:

1. A method of preventing fibrosis or cirrhosis of the liver in an animal in need thereof which comprises administering betaine to said animal in an amount of not less than about 1500 mg. per kg. of body weight per day.

2. The method of claim 1 wherein said animal is a rat.

3. The method of claim 1 wherein said animal is a human.

4. The method of claim 1 wherein said liver injury-causing condition is prolonged ethanol intake.

5. The method of claim 4 wherein said liver injury causing condition is alcoholism.

6. The method of claim 1 wherein said liver injury-causing condition is carbon tetrachloride exposure.

7. The method of claim 1 wherein said betaine is administered orally.

8. A method of preventing advanced liver damage in an animal exposed to liver injury causing conditions comprising:
   supplementing the diet of said animal with an amount of not less than 0.5% betaine so that said betaine will stimulate S-adenosylmethionine production.

9. The method of claim 8 wherein said betaine is in an amount of not less than 1500 mg per kg of body weight per day.

* * * * *